US011576893B2

(12) United States Patent
Löscher et al.

(10) Patent No.: US 11,576,893 B2
(45) Date of Patent: Feb. 14, 2023

(54) PHARMACEUTICAL COMPOSITIONS COMPRISING NEBIVOLOL

(71) Applicant: NOVALIQ GMBH, Heidelberg (DE)

(72) Inventors: Frank Löscher, Schriesheim (DE); Kirsten Eickhoff, Aschaffenburg (DE); Diana Strehl, Heidelberg (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 16/977,368

(22) PCT Filed: Mar. 1, 2019

(86) PCT No.: PCT/EP2019/055149
§ 371 (c)(1),
(2) Date: Sep. 1, 2020

(87) PCT Pub. No.: WO2019/166631
PCT Pub. Date: Sep. 6, 2019

(65) Prior Publication Data
US 2021/0106558 A1 Apr. 15, 2021

Related U.S. Application Data

(60) Provisional application No. 62/637,676, filed on Mar. 2, 2018.

(30) Foreign Application Priority Data

Mar. 2, 2018 (EP) .................................. 18159727

(51) Int. Cl.
| | |
|---|---|
| *A61K 31/353* | (2006.01) |
| *A61P 27/06* | (2006.01) |
| *A61K 9/00* | (2006.01) |
| *A61K 9/14* | (2006.01) |
| *A61K 47/06* | (2006.01) |

(52) U.S. Cl.
CPC .......... *A61K 31/353* (2013.01); *A61K 9/0048* (2013.01); *A61K 9/145* (2013.01); *A61K 47/06* (2013.01); *A61P 27/06* (2018.01)

(58) Field of Classification Search
CPC ...... A61K 31/353; A61K 9/145; A61K 47/06; A61K 9/0048; A61P 27/06
See application file for complete search history.

(56) References Cited

U.S. PATENT DOCUMENTS

| | | | |
|---|---|---|---|
| 2,616,927 A | 11/1952 | Kauck et al. | |
| 4,452,818 A | 6/1984 | Haidt | |
| 5,077,036 A | 12/1991 | Long, Jr. | |
| 5,326,566 A | 7/1994 | Parab | |
| 5,336,175 A | 8/1994 | Mames | |
| 5,370,313 A | 12/1994 | Beard | |
| 5,518,731 A | 5/1996 | Meadows | |
| 5,667,809 A | 9/1997 | Trevino | |
| 5,874,469 A | 2/1999 | Maniar et al. | |
| 5,874,481 A | 2/1999 | Weers | |
| 5,904,933 A | 5/1999 | Riess et al. | |
| 5,980,936 A | 11/1999 | Krafft et al. | |
| 5,981,607 A | 11/1999 | Ding | |
| 6,042,845 A | 3/2000 | Sun et al. | |
| 6,060,085 A | 5/2000 | Osborne | |
| 6,113,919 A | 9/2000 | Cronelus | |
| 6,140,374 A | 10/2000 | Ma et al. | |
| 6,159,977 A | 12/2000 | Reeves | |
| 6,177,477 B1 | 1/2001 | George et al. | |
| 6,197,323 B1 | 3/2001 | Georgieff | |
| 6,224,887 B1 | 5/2001 | Samour et al. | |
| 6,262,126 B1 | 7/2001 | Meinert et al. | |
| 6,294,563 B1 | 9/2001 | Garst | |
| 6,335,335 B2 | 1/2002 | Higashiyama | |
| 6,372,243 B2 | 4/2002 | Kobuch et al. | |
| 6,391,879 B1 | 5/2002 | Reeves | |
| 6,399,087 B1 | 6/2002 | Zhang et al. | |
| 6,458,376 B1 | 10/2002 | Meadows | |
| 6,730,328 B2 | 5/2004 | Maskiewicz | |
| 7,001,607 B1 | 2/2006 | Menz | |
| 7,026,359 B1 | 4/2006 | Gross | |
| 7,041,705 B2 | 5/2006 | Mishra et al. | |
| 7,258,869 B1 | 8/2007 | Berry | |
| 7,687,455 B2 | 3/2010 | Bonnet et al. | |
| 7,740,875 B2 | 6/2010 | Dechow | |

(Continued)

FOREIGN PATENT DOCUMENTS

| | | |
|---|---|---|
| EP | 0 670 159 | 9/1995 |
| EP | 1 152 749 | 11/2001 |

(Continued)

OTHER PUBLICATIONS

Meinert H., et al., "Semifluorinated alkanes—a new class of compounds with outstanding properties for use in ophthalmology," European Journal of Ophthalmo, 10(3):189-197 (2000).
Szummy, et al., "The influence of new beta-adrenolytics nebivolol and carvedilol on intraocular pressure and iris blood flow in rabbits," Graefes Arch Clin Exp Ophthalmol 252:917-923 (2014).
Costa Gomes et al., "Solubility of dioxygen in seven fluorinated liquids," Journal of Fluorine Chemistry, 2004, 125:1325-1329.
Davies, "Biopharmaceutical Considerations in Topical Ocular Drug Delivery," Clin. Exper.Pharmacol. Physiol., 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbons," Fluid Phase Equilibria, 2004, 222-223:325-330.

(Continued)

*Primary Examiner* — Genevieve S Alley
(74) *Attorney, Agent, or Firm* — Hoxie & Associates LLC

(57) ABSTRACT

The present invention relates to pharmaceutical compositions comprising the selective beta 1 (B1)-receptor blocker nebivolol and/or a pharmaceutically acceptable salt thereof and a liquid vehicle comprising a semifluorinated alkane. The pharmaceutical composition of the present invention is useful for topical administration, for example ophthalmic topical administration and for use in the treatment of glaucoma, increased intraocular pressure, ocular hypertension and/or a symptom associated therewith.

21 Claims, 2 Drawing Sheets

(56) References Cited

U.S. PATENT DOCUMENTS

| | | |
|---|---|---|
| 7,776,349 B2 | 8/2010 | Dechow |
| 8,029,977 B2 | 10/2011 | Meinert et al. |
| 8,470,873 B2 | 6/2013 | Chen |
| 8,492,334 B2 | 7/2013 | Lavik et al. |
| 8,614,178 B2 | 12/2013 | Theisinger et al. |
| 8,618,093 B2 | 12/2013 | Chen et al. |
| 8,759,404 B2 | 6/2014 | Daftary et al. |
| 8,772,337 B2 | 7/2014 | Pilotaz et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Wilson |
| 9,757,459 B2 | 9/2017 | Theisinger et al. |
| 9,757,460 B2 | 9/2017 | Gunther et al. |
| 9,770,508 B2 | 9/2017 | Gunther et al. |
| 9,968,678 B2 | 5/2018 | Theisinger et al. |
| 10,045,996 B2 | 8/2018 | Theisinger et al. |
| 10,058,615 B2 | 8/2018 | Gunther et al. |
| 10,064,944 B2 | 9/2018 | Wilson et al. |
| 10,123,904 B2 | 11/2018 | Chauhan et al. |
| 10,130,707 B2 | 11/2018 | Günther et al. |
| 10,273,298 B2 | 4/2019 | Günther et al. |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 11,154,513 B2 | 10/2021 | Scherer et al. |
| 11,160,865 B2 | 11/2021 | Theisinger et al. |
| 2001/0038859 A1 | 11/2001 | Maskiewicz et al. |
| 2002/0004063 A1 | 1/2002 | Zhang |
| 2003/0018044 A1 | 1/2003 | Pervnan |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson |
| 2005/0075407 A1 | 4/2005 | Tamarkin et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0009522 A1 | 1/2006 | Dana et al. |
| 2006/0153905 A1 | 7/2006 | Carrara et al. |
| 2007/0238732 A1 | 10/2007 | Graham et al. |
| 2008/0019926 A1 | 1/2008 | Krafft et al. |
| 2008/0050335 A1 | 2/2008 | Faour et al. |
| 2008/0089923 A1 | 4/2008 | Burkstrand et al. |
| 2008/0207537 A1 | 8/2008 | Turner et al. |
| 2008/0254106 A1 | 10/2008 | Bell |
| 2008/0260656 A1 | 10/2008 | Mallard |
| 2009/0149546 A1 | 6/2009 | Chang |
| 2010/0006600 A1 | 1/2010 | Dascanio |
| 2010/0016814 A1 | 1/2010 | Gokhale et al. |
| 2010/0189765 A1 | 7/2010 | Erikson et al. |
| 2010/0226997 A1 | 9/2010 | Bowman et al. |
| 2010/0274215 A1 | 10/2010 | Wong et al. |
| 2011/0223208 A1 | 9/2011 | Hill et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2013/0084250 A1 | 4/2013 | Hagedorn et al. |
| 2013/0336557 A1 | 12/2013 | Cruzat et al. |
| 2014/0004197 A1 | 1/2014 | Theisinger et al. |
| 2016/0000941 A1 | 1/2016 | Keller et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2018/0360908 A1 | 12/2018 | Beier et al. |
| 2019/0274970 A1 | 9/2019 | Günther et al. |
| 2019/0328717 A1 | 10/2019 | Günther et al. |
| 2019/0343793 A1 | 11/2019 | Günther et al. |
| 2020/0060987 A1 | 2/2020 | Günther et al. |
| 2020/0129543 A1 | 4/2020 | Löscher et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0268648 A1 | 8/2020 | Günther et al. |
| 2020/0268682 A1 | 8/2020 | Günther et al. |
| 2020/0338015 A1 | 10/2020 | Scherer et al. |
| 2021/0023166 A1 | 1/2021 | Löscher et al. |
| 2021/0069014 A1 | 3/2021 | Löscher et al. |
| 2021/0121471 A1 | 4/2021 | Löscher et al. |
| 2021/0228595 A1 | 7/2021 | Löscher et al. |
| 2021/0236591 A1 | 8/2021 | Leo et al. |
| 2021/0315832 A1 | 10/2021 | Scherer et al. |
| 2021/0346313 A1 | 11/2021 | Beier et al. |
| 2022/0008397 A1 | 1/2022 | Xu et al. |

FOREIGN PATENT DOCUMENTS

| | | |
|---|---|---|
| EP | 2 462 921 | 11/2010 |
| JP | S6452722 | 2/1989 |
| JP | 2001/158734 | 6/2001 |
| JP | 2011/006348 | 1/2011 |
| WO | WO 1998/005301 | 12/1998 |
| WO | WO 00/545 88 | 9/2000 |
| WO | WO 2003/099258 | 12/2003 |
| WO | WO 2008/136034 | 11/2008 |
| WO | WO 2010/146536 | 12/2010 |
| WO | WO 2016/082644 | 6/2016 |
| WO | WO 2016/108130 | 7/2016 |
| WO | WO 2017/210158 | 12/2017 |

OTHER PUBLICATIONS

Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).

English-language machine translation of EP0670159 (A1) issued in U.S. Appl. No. 14/122,025, filed Apr. 1, 2015, 10 pages.

Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.

Gehlsen et al., "A semifluorinated alkane (F4H5) as novel carrier for cyclosporine A: a promising therapeutic and prophylactic option fortopical treatment of dry eye," Graefe's Arch. Clin.Exp, Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).

Gerdenitsch, "Emulsions—established and promising drug carriers for parenteral administration," retrieved from Internet, date accessed: Jun. 20, 2016, 2 pages URL: <http:/ipimediaworld.com/wp-content/uploads/2012/05/Pages-from-IPI-volume2-Issue-1-11.pdf.>.

German, E.J., et al., "Reality of drop size from multi-dose eye drop bottles: is it cause for concern?" Eye, 1999, 13:93-100.

Hardung, H., "Semifluorierte und perfluorierte Vergindungen zur topischen und parenteralenAnwendung," 2008, 188 pages, retrieved from Internet, date accessed: Oct. 10, 2011, URL: <http://www.freidok.uni-freiburg.de/volltexte/5682/pdf/Dissertation Hardung.pelf>.

Hardung, H., "Semifluorierte und perfluorierte Verbindungen zur topischen und parenteralenAnwendung," 2008, English Langnage Abstract, 2 pages, retrieved from https://freidok.uni-freiburg.de/data/5682 (retrieved on Jul. 10, 2017).

Holm, R. et al., "A novel excipient, 1-perfluorohexyloctane shows limited utility for the oral delivery of poorly water-soluble drugs," European Journal of Pharmaceutical Sciences, 2011, 42:416-422.

(56) References Cited

OTHER PUBLICATIONS

JPS6452722, English Machine Translation of the Abstract, Description, and Claims, Espacenet, Date Accessed: Feb. 10, 2016, 4 pages.

Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Messmer et al., "Semifluorierte Alkane als Therapie bei Meibomdriisen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

O'Rourke, M. et al., "Enhancing Delivery of Topical Ocular Drops," Cataract & Refractive Surgery Today Europe, 2016, 2 pages.

Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.

Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

Wong et al., "Perfluorocarbons and Semifluorinated Alkanes," Seminars in Ophthalmology; vol. 15 (1), 2000, p. 25-35.

PHARMACEUTICAL COMPOSITIONS COMPRISING NEBIVOLOL

CROSS-REFERENCE TO RELATED APPLICATIONS

This Application is a U.S. National Stage Application filed under 35 U.S.C. § 371 which claims priority to and the benefit of International Application No. PCT/EP2019/055149, filed on Mar. 1, 2019, which claims priority to U.S. Provisional Application No. 62/637,676, filed on Mar. 2, 2018, and European Application No. 18159727.9, filed on Mar. 2, 2018, the contents of each of which are hereby incorporated by reference in their entireties.

BACKGROUND

The present invention relates to a pharmaceutical composition comprising the selective beta 1 ($\beta_1$)-receptor blocker nebivolol and a liquid vehicle comprising a semifluorinated alkane. The pharmaceutical composition of the present invention is useful for topical administration, especially ophthalmic topical administration.

Pharmaceutical compositions in liquid form represent one of the preferred types of drug formulations. Certain routes of topical administration, such as ophthalmic administration, typically require the liquid form in order to provide for an efficient delivery of the active ingredient and a patient-friendly mode of use.

The simplest type of liquid formulation is a solution, such as an aqueous solution of the active pharmaceutical ingredient. In certain cases, however, the development of a more complex formulation such as a suspension may be considered. For example, if a drug substance is very poorly soluble in aqueous or other biocompatible solvent systems, or if it is hydrolytically labile, a simple solution may not be feasible or represent the best choice.

Nebivolol belongs to a class of compounds named beta-blockers—a class of medications that are used to manage abnormal heart rhythms and to protect the heart from a second heart attack after a first heart attack (secondary prevention). They are also widely used to treat high blood pressure (hypertension).

Beta-blockers are also used in the treatment of glaucoma. Beta-blockers act by blocking beta-receptors at the level of the ciliary body and by reducing the aqueous humour production, thereby reducing the intraocular pressure (IOP). Two types of topical beta-blockers are available for use in the treatment of glaucoma: Non-selective beta-blockers, which block both beta 1 ($\beta_1$)- and beta 2 ($\beta_2$)-adrenoceptors; and cardio-selective beta blockers, which block only beta 1-receptors. Of the beta-blockers commercially available, timolol, levobunolol, metipranolol and carteolol are nonselective; betaxolol is a cardio-selective beta-blocker. The most serious side effects of beta-blockers are the exacerbation of chronic obstructive airways disease with nonselective agents and the precipitation of bronchospasm in some patients.

Nebivolol is a beta 1 ($\beta_1$)-receptor blocker with nitric oxide-potentiating vasodilatory effect used in treatment of hypertension and also for left ventricular failure. It is highly cardio-selective under certain circumstances. It is therapeutically used in form of a racemic mixture of its hydrochloride salt and displays negative inotropic as well as direct vasodilating activity.

Increased intraocular pressure is a frequent disorder of the eye which is often associated with optic nerve damage, in which case the disease is glaucoma. In the absence of optic nerve damage, the condition is referred to as ocular hypertension.

Normal intraocular pressure is usually defined as being in the range from 10 to 21 mmHg. The pressure results predominantly from balance between the production rate and the drainage rate of the aqueous humour in the eye. In addition, it is influenced by the corneal thickness and rigidity. The intraocular pressure typically fluctuates around about 15 to 16 mmHg with amplitudes of up to 6 mmHg. For example, it usually decreases in the night due to a decreased production of aqueous humour. It also responds to various physiological factors such as exercise, heart rate, respiration, fluid intake, as well as certain types of systemic or topical drugs.

The aqueous humour is produced by the ciliary bodies of the eye, from where it flows into the posterior chamber. The composition of the aqueous humour is very similar to that of blood plasma but differs from the latter by a lower protein content. Its main constituents are water (99%), electrolytes (inorganic ions to maintain the physiological pH), low amounts of albumin and $\beta$-globulins, ascorbate, glucose, lactate, and amino acids.

From the posterior chamber, the aqueous humour is distributed via the pupil of the iris into the anterior chamber of the eye. From here, it flows through the so-called trabecular meshwork, which is a spongy tissue area lined by trabeculocytes whose main function is to drain the humour into a set of tubes called Schlemm's canal, from where the humour enters the blood circulation. The humour flow from the trabecular meshwork into the Schlemm's canal occurs via two different routes: either directly via the aqueous vein to the episcleral vein, or indirectly via collector channels to the episcleral vein by intrascleral plexus. This trabecular outflow pathway accounts for the major fraction of drained aqueous humour. In addition, there exists a second major drainage pathway which is the uveoscleral outflow, which is relatively independent of the intraocular pressure and normally accounts for only 5 to 10% of the aqueous humour drainage in healthy humans.

WO2008/136034 A2 describes the use of nebivolol or a salt or an ester thereof for the production of a medicament for lowering ocular hypertension. Nebivolol is formulated as an emulsion comprising, among others, soybean oil, egg yolk phospholipids and glycerol; as an oil solution comprising soybean oil; and as an ophthalmic ointment comprising liquid paraffine and vaseline. In animal studies the animals are treated with 100 µl 1% nebivolol in emulsion per eye.

D. Szummy et al. describe in Graefes Arch Clin Exp Ophthalmol (2014) 252:917-923 experiments in which the effect of nebivolol on intraocular pressure is studied. Therein, solutions of nebivolol are administered orally or topically into a conjunctival sac of a rabbits' eyes. The nebivolol solutions are administered in concentrations of 0.1%, 0.5% and 1% in a volume of 1 drop (50 µl). No indication is given, however, regarding the exact composition of the solution, especially not with regard to the solvent used.

WO2016/108130 A1 describes in the experimental section dispersions of nebivolol hydrochloride in paraffin and the preparation of gels comprising nebivolol hydrochloride for the treatment of diabetic wounds.

As an alternative to aqueous preparations, oily eye drops may be formulated if the respective drug substance is poorly water-soluble or prone to hydrolytic degradation. However, one of the major disadvantages of all oil-based formulations for ophthalmic administration is that they inherently have a negative impact on vision. Whether used as oily solutions or oil-in-water emulsions, they exhibit a refractive index which differs substantially from that of physiological tear fluid, which leads to visual disturbances and blurring.

Moreover, oil-based formulations do not readily mix with tear fluid to form a homogenous liquid phase. Oily solutions are altogether immiscible with the aqueous tear fluid, and the exact fate of an emulsion mixed with tear fluid in a physiological setting is not completely predictable. Further, oily carrier such as medium chain triglycerides (MCT) are known to cause a strong burning sensation upon instillation to the eye.

Furthermore, oil-in-water emulsions are like aqueous solutions prone to microbial contamination during use. If they were to be presented in multi-dose containers which are in principle more cost-efficient and convenient for patients than single-use vials, they would have to be preserved in order to ensure their microbiological quality. At the same time, preservatives which can be used in ophthalmic formulations are potentially damaging to the eye, in particular to the ocular surface, and should be avoided whenever possible.

It is therefore an object of the present invention to provide a novel pharmaceutical formulation comprising nebivolol and/or a pharmaceutically acceptable salt thereof, which can be useful as a medicament, particularly for topical applications. It is a further object of the present invention to find a treatment of increased intraocular pressure, e.g. in association with open-angle glaucoma or ocular hypertension, which overcomes at least one of the limitations or disadvantages associated with prior art formulations.

A further object of the present invention is to provide liquid formulations of nebivolol and/or a pharmaceutically acceptable salt thereof which shows advantageous long-term stability.

A further object of the present invention is to provide liquid formulations of nebivolol and/or a pharmaceutically acceptable salt thereof which is effective in decreasing intraocular pressure at reduced target dosage.

Further objects of the invention will become clear on the basis of the following description, examples, and patent claims.

SUMMARY OF THE INVENTION

In a first aspect, the present invention provides a pharmaceutical composition comprising:
(a) nebivolol and/or a pharmaceutically acceptable salt thereof, and
(b) a liquid vehicle comprising a semifluorinated alkane.

In a second aspect, the present invention provides the composition of the first aspect of the invention for use as medicament, more specifically for the treatment of glaucoma, increased intraocular pressure, ocular hypertension and/or a symptom associated therewith.

In a further aspect, the present invention provides a method for the treatment of glaucoma, increased intraocular pressure, ocular hypertension and/or a symptom associated therewith, comprising administering to the eye of a subject in need thereof a pharmaceutical composition according to the first aspect of the present invention.

In yet a further aspect, the present invention provides a kit comprising the pharmaceutical composition according to the first or second aspect of the invention and a container for holding the pharmaceutical composition.

DETAILED DESCRIPTION OF THE INVENTION

Figure 1:
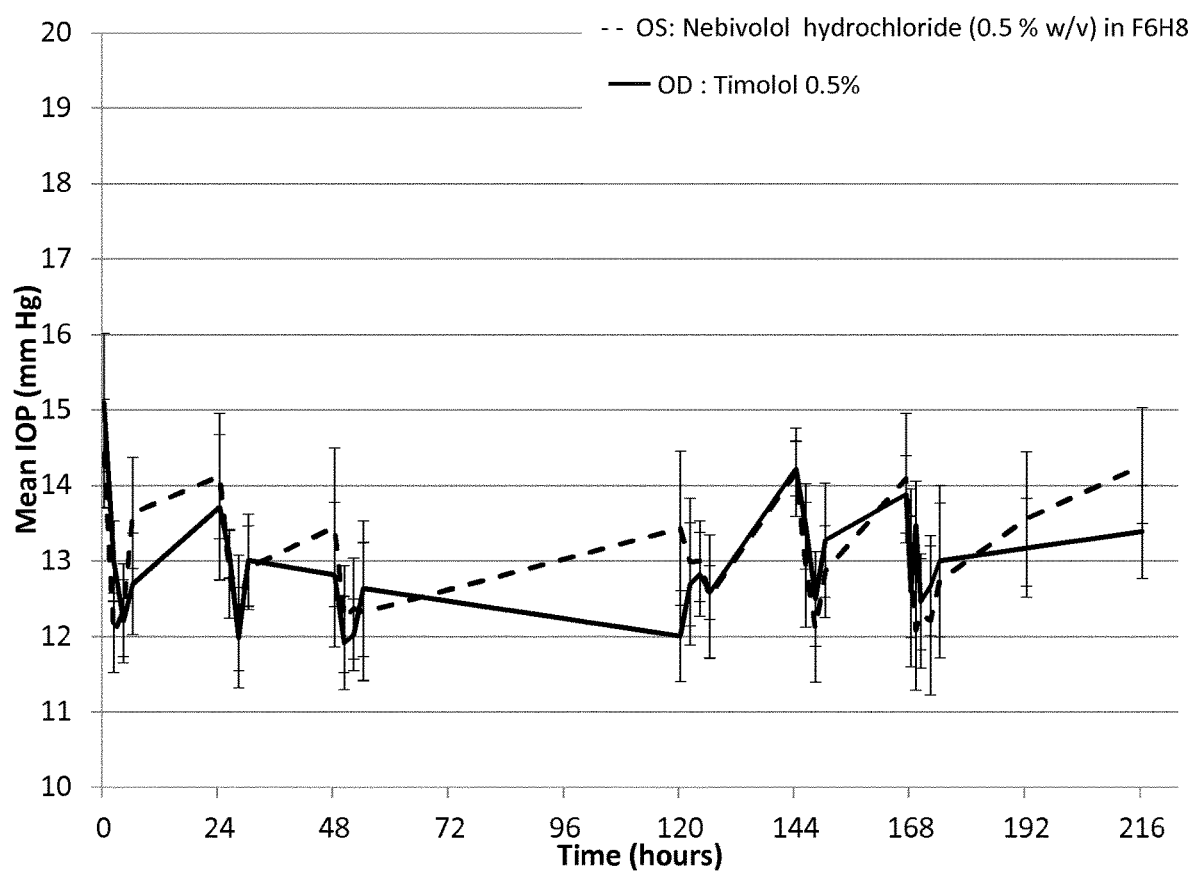
FIG. 1 is a graphical representation of the results of the measurement of the in-vivo intraocular pressure study according to Example 4 below in which a suspension of nebivolol hydrochloride at a concentration of 0.5% (w/v) in 1-perfluorohexyl-octane (F6H8) is administered.

It has been found by the inventors that the composition of the invention surprisingly overcomes several drawbacks of previously known formulations of nebivolol.

In a first aspect, the present invention provides a pharmaceutical composition comprising:
(a) nebivolol and/or a pharmaceutically acceptable salt thereof, and
(b) a liquid vehicle comprising a semifluorinated alkane.

The pharmaceutical composition according to the present invention comprises as a first constituent (a) nebivolol and/or a pharmaceutically acceptable salt of nebivolol. The compound nebivolol as used herein is the secondary amine 1,1'-[Bis(6-fluoro-3,4-dihydro-2H-1-benzopyran-2-yl)]-2,2'-iminodiethanol of structural formula (Ia)

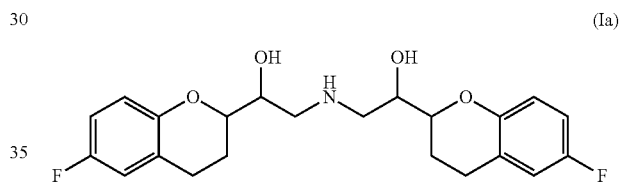

(Ia)

with the molecular formula $C_{22}H_{25}F_2NO_4$, molecular mass of 405.44 g/mol. The compound is also known as narbivolol or nebivololum and may be used in the form of a mixture of diastereomers or in the form of single diastereomers, such as, for example, the diastereomer of formula (Ib)

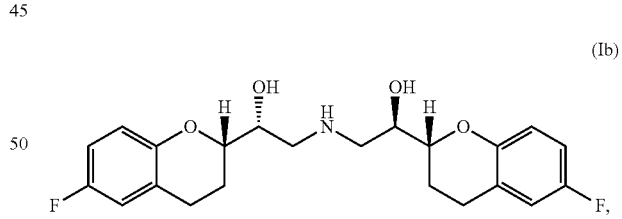

(Ib)

either in form of racemic mixtures of said diastereomers, or in the form of non-racemic mixtures or in the form of pure enantiomers, such as, for example, in the form of the RSSS and SRRR enantiomers.

The term nebivolol as used herein may refer to a racemic mixture of enantiomers, to any non-racemic, i.e. enantiomerically enriched mixtures, as well as single diastereomers, or mixtures of diastereomers of the compound of formula (Ia), which may be used for the preparation of the pharmaceutical composition of the present invention as available and in accordance with its intended use.

Nebivolol is commercially available in form of its free base as described and shown by formula (Ia) and (Ib) above as well as in the form of pharmaceutically acceptable salts such as, for example nebivolol hydrochloride of formula (Ic)

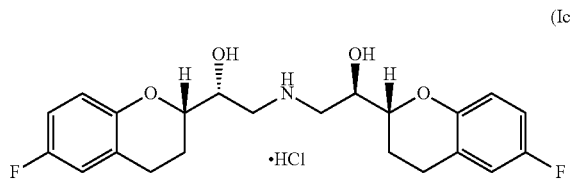

or other pharmaceutically acceptable addition salts.

The pharmaceutical composition may comprise nebivolol and/or a pharmaceutically acceptable salt of nebivolol which means that the composition may comprise nebivolol in form of its free base as, for example shown in formula (Ia) and formula (Ib), either alone or in combination with one or a mixture of different pharmaceutically acceptable salts of nebivolol. Furthermore, the present pharmaceutical composition may comprise nebivolol in form of a salt, such as the hydrochloride of formula (Ic) either alone or in form of a mixture with other pharmaceutically acceptable salts of nebivolol as described above.

In a preferred embodiment of the present invention, however, the pharmaceutical composition of the present invention comprises nebivolol in form of nebivolol hydrochloride salt. Preferably, the pharmaceutical composition of the present invention comprises as component a) nebivolol hydrochloride salt as a racemic mixture of the stereoisomer of formula (Ic) and its enantiomer.

Preferably, the nebivolol, nebivolol hydrochloride or another pharmaceutically acceptable salt of nebivolol as described above is present in the pharmaceutical compositions according to present invention in a therapeutically effective amount. The term "a therapeutically effective amount" as used herein refers to a dose, concentration or strength which is useful for producing a desired pharmacological effect.

As a second constituent (b), the pharmaceutical composition according to the present invention comprises a liquid vehicle comprising a semifluorinated alkane. Some of the key advantages of the present invention are brought about by the presence of a semifluorinated alkane in the composition, functioning as a liquid vehicle for forming either a solution, dispersion or a suspension. The term 'semifluorinated alkane' as used herein means a compound in which a perfluorinated linear or branched, preferably linear hydrocarbon segment is attached to a linear or branched, preferably linear hydrocarbon segment.

In preferred embodiments, however, the pharmaceutical composition of the present invention or, more specifically, the liquid vehicle of the pharmaceutical composition of the present invention comprises a semifluorinated alkane of the general formula (II)

$$CF_3(CF_2)_n(CH_2)_mCH_3 \qquad (II),$$

wherein the index n is an integer selected from 2 to 10, and m is an integer selected from 2 to 10; or wherein n is an integer selected from 3 to 7 and m is an integer selected from 4 to 7. Preferably, the liquid vehicle of the pharmaceutical composition of the present invention comprises a semifluorinated alkane of the general formula (II) wherein the index n is an integer selected from 3 to 5, and m is an integer selected from 4 to 7.

Accordingly, said semifluorinated alkane as used in the composition of the present invention may preferably be selected from $CF_3(CF_2)_3$—$(CH_2)_4CH_3$ (F4H5), $CF_3(CF_2)_3$—$(CH_2)_5CH_3$ (F4H6), $CF_3(CF_2)_3$—$(CH_2)_6CH_3$ (F4H7), $CF_3(CF_2)_3$—$(CH_2)_7CH_3$ (F4H8), $CF_3(CF_2)_4$—$(CH_2)_4CH_3$ (F5H5), $CF_3(CF_2)_4$—$(CH_2)_5CH_3$ (F5H6), $CF_3(CF_2)_4$—$(CH_2)_6CH_3$ (F5H7), $CF_3(CF_2)_4$—$(CH_2)_7CH_3$ (F5H8), $CF_3(CF_2)_5$—$(CH_2)_4CH_3$ (F6H5), $CF_3(CF_2)_5$—$(CH_2)_5CH_3$ (F6H6), $CF_3(CF_2)_5$—$(CH_2)_6CH_3$ (F6H7), $CF_3(CF_2)_5$—$(CH_2)_7CH_3$ (F6H8), $CF_3(CF_2)_7$—$(CH_2)_7CH_3$ (F8H8), $CF_3(CF_2)_5$—$(CH_2)_9CH_3$ (F6H10). More preferably, said semifluorinated alkane may be selected from $CF_3(CF_2)_3$—$(CH_2)_4CH_3$ (F4H5), $CF_3(CF_2)_5$—$(CH_2)_5CH_3$ (F6H6), $CF_3(CF_2)_5$—$(CH_2)_7CH_3$ (F6H8) and $CF_3(CF_2)_5$—$(CH_2)_9CH_3$ (F6H10). Most preferably, said semifluorinated alkane is one selected from $CF_3(CF_2)_3$—$(CH_2)_4CH_3$ (F4H5) and $CF_3(CF_2)_5$—$(CH_2)_7CH_3$ (F6H8).

An alternative nomenclature for the specified semifluorinated alkanes as noted in parentheses below and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-fluorobutyl-pentane or $CF_3(CF_2)_3$—$(CH_2)_4CH_3$ (which may be also, alternatively expressed as formula $F(CF_2)_4(CH_2)_5H$), which has a linear perfluorinated segment F with four carbons (n=4) and a linear non-fluorinated hydrocarbon segment with five carbons (m=5). Furthermore, F6H8 may be used to denote 1-perfluorohexyl-octane or $CF_3(CF_2)_5$—$(CH_2)_7CH_3$ (which may be also, alternatively expressed as formula $F(CF_2)_6(CH_2)_8H$), which has a linear perfluorinated segment F with six carbons (n=6) and a linear non-fluorinated hydrocarbon segment with 8 carbons (m=8).

The pharmaceutical composition of the invention comprising of "a" semifluorinated alkane is to be understood herein, as comprising at least one semifluorinated alkane of Formula (II) as described above. Optionally, however, the composition may comprise of more than one, for example, a mixture of two or more semifluorinated alkanes of Formula (II), i.e. of any one of the semifluorinated alkane species as described above.

In a preferred embodiment, the pharmaceutical composition according to the present invention comprises a semifluorinated alkane of Formula (II) which is selected from 1-perfluorohexyl-octane ($CF_3(CF_2)_5$—$(CH_2)_7CH_3$ (F6H8)) and 1-perfluorobutyl-pentane ($CF_3(CF_2)_3$—$(CH_2)_4CH_3$ (F4H5)). In a particular preferred embodiment of the present invention, the semifluorinated alkane of Formula (II) is perfluorohexyl-octane ($CF_3(CF_2)_5(CH_2)_7CH_3$, F6H8).

In yet a further embodiment, the liquid vehicle of the pharmaceutical composition of the present invention may consist of a semifluorinated alkane of Formula (II) as specified above. In this context also, the term "a" semifluorinated alkane is to be understood as at least one semifluorinated alkane, but may also include the option of more than one, or a plurality of semifluorinated alkane compounds. Accordingly, in one embodiment, the composition may consist of more than one semifluorinated alkane of Formula (II) as specified above.

In another embodiment, the pharmaceutical composition according to the present invention comprises (a) nebivolol and/or a pharmaceutically acceptable salt thereof, and (b) a liquid vehicle comprising or essentially consisting of a semifluorinated alkane of general formula (II) as defined above, or a semifluorinated alkane selected from any one, or combination of the semifluorinated alkane compounds as defined above, and optionally, (c) one or more excipients.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of'). It is to be understood that isomeric or olefinic impurities that originate from synthesis of semifluorinated alkanes and that are present in only trace or residual amounts, as these cannot be quantitatively removed upon purification, and that do not confer any technical advantage or relevance in respect of the object of the present invention, do fall under the above definition of such other constituent or component. In contrast, the term 'comprising" or related terms "comprises" or "comprise" in the context of the present compositions, is to be understood as meaning that other features, other than those prefaced by the term may be present in the composition.

In a further embodiment, the liquid vehicle of the present pharmaceutical compositions as defined in any of the previous embodiments described above, preferably comprises a semifluorinated alkane or optionally, a mixture of semifluorinated alkanes in an amount of at least 70% (w/w), 75% (w/w), 85% (w/w), 90% (w/w), 95% (w/w), 98% (w/w), 98.5% (w/w), 99% (w/w), 99.5% (w/w), 99.8% (w/w) or at least 99.9% (w/w) of a semifluorinated alkane or a mixture of semifluorinated alkanes as described above, with respect to the total weight of the liquid vehicle.

In some embodiments, the liquid vehicle of the present pharmaceutical composition comprises at least 85% (w/w) of a semifluorinated alkane or a mixture of different semifluorinated alkanes. In a further embodiment, the liquid vehicle of the present invention essentially consists of 100% (w/w) of a semifluorinated alkane or mixture of semifluorinated alkanes.

The term "% (w/w)" as used herein and unless indicated otherwise refers to the amount of a component of a composition as a weight percentage in relation to the total weight of the liquid vehicle of the present pharmaceutical composition (with 'w' denoting weight).

In a particularly preferred embodiment, the liquid vehicle of the pharmaceutical composition according to the present invention comprises 1-perfluorohexyl-octane ($CF_3(CF_2)_5$—$(CH_2)_7CH_3$ (F6H8)), preferably as the only semifluorinated alkane present in the pharmaceutical composition. In a further preferred embodiment, the liquid vehicle of the pharmaceutical composition of the present invention essentially consists of 1-perfluorohexyl-octane (F6H8). It is understood that a liquid vehicle essentially consisting of 1-perfluorohexyl-octane may comprise in trace or residual amounts isomeric or olefinic impurities (such as 2-perfluorohexyl-octane or 1-perfluorohexyl-octene) originating from synthesis of F6H8 which cannot be quantitatively removed upon purification.

In further embodiments, the liquid vehicle of the pharmaceutical composition according to the present invention comprises 1-perfluorobutyl-pentane ($CF_3(CF_2)_3$—$(CH_2)_4CH_3$ (F4H5)), preferably as the only semifluorinated alkane present in the pharmaceutical composition. In a further preferred embodiment, the liquid vehicle of the pharmaceutical composition of the present invention essentially consists of 1-perfluorobutyl-pentane (F4H5). It is understood that a liquid vehicle essentially consisting of 1-perfluorobutyl-butane may comprise in trace or residual amounts isomeric or olefinic impurities (such as 2-perfluorobutyl-pentane or 1-perfluorobutyl-pentene) originating from synthesis of F4H5 which cannot be quantitatively removed upon purification.

The liquid semifluorinated alkanes as described above are chemically and physiologically inert, colourless and stable. Their typical densities range from 1.1 to 1.7 g/cm$^3$, and their surface tension may be as low as 19 mN/m. Semifluorinated alkanes of the RFRH type are insoluble in water but also somewhat amphiphilic, with increasing lipophilicity correlating with an increasing size of the non-fluorinated segment.

The liquid vehicle of the pharmaceutical composition comprising a semifluorinated alkane as described above may also comprise a further solubilizing agent, such as one or more solvents or co-solvents. In specific embodiments, the liquid vehicle of the present pharmaceutical composition comprises a co-solvent, preferably an organic co-solvent.

As used herein, the term "solubilizing agent" may denote a compound or solvent or a co-solvent, preferably an organic solvent, that is miscible with the semifluorinated alkane or the mixture of different semifluorinated alkanes of the present liquid vehicle and that enhances or facilitates the solubility, or the dispersability of the active component nebivolol in the chosen liquid vehicle comprising a semifluorinated alkane as described above.

Examples of potentially useful organic co-solvents include glycerol, propylene glycol, polyethylene glycol, and ethanol. However, the concentration of the co-solvent should preferably be low relative to that of the semifluorinated alkane or semifluorinated alkane mixture. If an organic co-solvent such as ethanol is used, it is recommendable to keep it at or below a level of approx. 10% (w/w) or 5% (w/w) or even 3% (w/w) with regard to the total weight of the liquid vehicle. More preferably, the content of the co-solvent, more specifically of ethanol is from about 0.1 to about 2% (w/w), and most preferably not more than about 1% (w/w) with regard to the total weight of the liquid vehicle. In some embodiments, the liquid vehicle of the present composition according to the invention, however, are free of an organic co-solvent.

In other embodiments, the solubilizing agent, that may be optionally comprised by the liquid vehicle of the present pharmaceutical composition, may preferably be present in an amount of up to 3% (w/w), or preferably of up to 2.5% (w/w) with respect to the total weight of the liquid vehicle. In a preferred embodiment, the liquid vehicle comprises a solubilising agent in amounts as low as up to 1% (w/w), preferably up to 0.5% (w/w) with respect to the total weight of the liquid vehicle. In another preferred embodiment, the liquid vehicle further comprises a solubilising agent in an amount of from about 2.5% to 0.5% (w/w), preferably of from about 1% to 0.5% (w/w) with respect to the weight of the liquid vehicle.

In some embodiments, the solubilizing agent may be a liquid excipient such as, for example, a further organic co-solvent as described above and/or an oil selected from glyceride oils, liquid waxes and liquid paraffin, or an organic solvent exhibiting a high degree of biocompatibility.

Examples of potentially useful liquid excipients comprise oily excipients which may be used in combination with one or more semifluorinated alkanes and include triglyceride oils, mineral oil, medium chain triglycerides (MCT), oily fatty acids isopropyl myristate, oily fatty alcohols, esters of sorbitol and fatty acids, oily sucrose esters or any other substance which is physiologically tolerated by the eye. In one of the preferred embodiment, the liquid vehicle comprises a solubilizing agent in form of a liquid excipient. Further examples of potentially useful solubilizing agents as used herein are organic solvents. Preferred organic solvents include glycerol, propylene glycol, polyethylene glycol and ethanol. In yet further preferred embodiments, the liquid vehicle of the present pharmaceutical composition may comprise ethanol as the solubilizing agent, preferably in an amount of up to 1% (w/w), more preferably of up to 0.8% (w/w) and most preferred of up to 0.5% (w/w) with regard to the total weight of the liquid vehicle of the present pharmaceutical composition.

The pharmaceutical composition of the present invention comprises, as a constituent a), the active ingredient nebivolol and/or a pharmaceutically acceptable salt thereof, preferably nebivolol hydrochloride, as described above. The present pharmaceutical composition may comprise nebivolol and/or a pharmaceutically acceptable salt thereof in an amount of from about 0.1% (w/v) to about 10% (w/v), or from about 0.1% (w/v) to about 5% (w/v), or from about 0.2% (w/v) to about 3% (w/v), or from about 0.2% (w/v) to about 2% (w/v), or from about 0.3% (w/v) to about 1.5% (w/v), or from about 0.4% (w/v) to about 1.25% (w/v), or from about 0.45% (w/v) to about 1.0% (w/v).

In preferred embodiments, the present pharmaceutical composition comprises nebivolol and/or a pharmaceutically acceptable salt thereof in an amount of from about 0.3% (w/v) to about 1.5% (w/v) or from about 0.45% (w/v) to about 1.0% (w/v).

In a further preferred embodiment, the present pharmaceutical composition comprises nebivolol hydrochloride in an amount of from about 0.3% (w/v) to about 1.5% (w/v) or from about 0.5% (w/v) to about 1.0% (w/v).

Unless otherwise indicated, the term "% (w/v)" as used throughout herein in connection with the present pharmaceutical composition denotes the amount of a component of a composition (such as, for example, nebivolol or nebivolol hydrochloride) as a weight percentage in relation to the total volume of the composition (with 'w' denoting the weight and 'v' denoting volume). For example, 0.05% (w/v) may be understood as relating to 0.5 mg of a component in 1 mL of the composition, and 0.1% (w/v) would correspond to 1.0 mg of a component in 1 mL of the composition.

The active component nebivolol and/or a pharmaceutically acceptable salt thereof, preferably nebivolol hydrochloride as described above may be dissolved, dispersed or suspended in the liquid vehicle comprising a semifluorinated alkane as described below. Accordingly, the liquid pharmaceutical composition of the present invention may be in the form of a solution, preferably a clear solution or in form of a suspension.

In preferred embodiments, the pharmaceutical composition of the present invention is provided in form of a suspension. A suspension may be defined as a type of a dispersion, a dispersion being a system having at least one continuous (or coherent) phase and at least one discontinuous (or inner) phase which is dispersed in the continuous phase. In a suspension, the dispersed phase is in the solid state. The suspensions useful for practising the present invention are liquids, at least at physiological temperature, which means that the continuous phase is a liquid. Typically, the suspensions are also liquid at room temperature.

Preferably, the present invention provides pharmaceutical compositions, in which particles of nebivolol and/or a pharmaceutically acceptable salt thereof, preferably particles of nebivolol hydrochloride, as the dispersed phase are suspended in a liquid vehicle comprising a semifluorinated alkane, for example, a semifluorinated alkane of formula (II) as defined above as the continuous phase. Accordingly, in preferred embodiments of the present invention, the nebivolol and/or a pharmaceutically acceptable salt thereof is suspended in the liquid vehicle comprising a semifluorinated alkane.

In further embodiment, the particles of nebivolol and/or a pharmaceutically acceptable salt thereof, preferably of nebivolol hydrochloride, are solid particles. In a further preferred embodiment, the particles, preferably the solid particles of nebivolol and/or a pharmaceutically acceptable salt thereof, preferably of nebivolol hydrochloride, substantially consist of nebivolol and/or a salt thereof, preferably of nebivolol hydrochloride.

In further embodiments, in the pharmaceutical composition of the present invention nebivolol and/or pharmaceutically acceptable a salt thereof, preferably of nebivolol hydrochloride, is suspended in the liquid vehicle at a concentration of from 0.3 to 1.5% (w/v) or preferably at a concentration of from 0.5 to 1.0% (w/v).

As outlined above, in preferred embodiments, nebivolol and/or a pharmaceutically acceptable salt thereof, preferably of nebivolol hydrochloride, as the active ingredient of the present pharmaceutical compositions is incorporated in the form of suspended solid particles. In a particular embodiment, the suspended particles largely or exclusively consist of the active ingredient.

The particle size of the suspended nebivolol particles, preferably particles of nebivolol or nebivolol hydrochloride is preferably below about 100 μm, which means that most of the particles, e.g. at least about 90% thereof, have a size below 100 μm. Which type of particle diameter is considered as particle size will depend on the method used for particle size distribution, which in turn is selected to be appropriate for the type of solid material and the approximate size range. For example, laser diffraction or dynamic light scattering (also known as photon correlation spectroscopy or quasi-elastic light scattering) are appropriate methods for determining particle sizes in the colloidal and low micron range, whereas sedimentation analysis, sieve analysis or photoanalysis may be selected for larger particle sizes.

In a further embodiment, at least about 90% of the suspended nebivolol and/or a pharmaceutically acceptable salt thereof have a particle size of not more than about 20 μm, preferably of not more than about 15 μm. In a most preferred embodiment, at least 90% of the suspended particles of nebivolol or a pharmaceutically acceptable salt thereof have a size lower than about 10 μm or have size lower than about 5 μm. Especially for ophthalmic administration, at least about 90% of the suspended particles of nebivolol and/or a pharmaceutically acceptable salt thereof have a size lower than about 20 μm, preferably with at least about 90% of the suspended particles having a size of not more than about 15 μm, more preferably of not more than about 10 μm, or preferably of not more than about 5 μm, as measured by state-of-the-art particle size distribution techniques (e.g. laser diffraction, dynamic light scattering).

The pharmaceutical composition comprising nebivolol and/or a pharmaceutically acceptable salt thereof, preferably nebivolol hydrochloride, especially when suspended in a liquid vehicle comprising a semifluorinated alkane display advantageous stability, especially with regard to the size of the suspended particles. As known from other pharmaceutical compositions in form of suspensions, the suspended particles may aggregate, and depending on the forces by which the particles attract each other, the aggregates thus formed may be rather difficult to resuspend. A further problem associated with that is that in suspensions having non-uniform particle sizes there is a tendency for smaller particles to gradually dissolve, whereas larger particles grow through the deposition of dissolved material onto their surfaces (Ostwald ripening). In result, the particle size distribution of a suspension may become broader over time. Particles which grow beyond a certain size may be unsuitable for the intended use; for example, they may occlude an injection cannula or, in case of ophthalmic administration, irritate or even damage the ocular surface.

In contrast to this, it was found that the pharmaceutical composition of the present invention comprising nebivolol and/or a pharmaceutically acceptable salt thereof, preferably nebivolol hydrochloride, especially when provided in form of a suspension can be stored for prolonged periods of time without significantly changing their particle size distribution. Accordingly, the pharmaceutical composition of the present invention comprising nebivolol and/or a salt thereof, preferably nebivolol hydrochloride, in form of a suspension may be stored for extended periods of time, such as, for example for up to 1 year, or up to 6 months, or up to 3 months, or up to 2 months or up to 1 month without significantly changing their particle size distribution of the suspended particles. In exemplary embodiments, the present invention provides a pharmaceutical composition comprising nebivolol and/or a salt thereof, preferably nebivolol hydrochloride, in form of a suspension wherein at least about 90% of the suspended particles of nebivolol and/or a pharmaceutically acceptable salt thereof have a size of not more than about 15 µm, after three weeks of storage at room temperature. The term room temperature as used herein is to be understood throughout as a temperature in the range of 20 to 25° C.

In another exemplary embodiment, the present invention provides a pharmaceutical composition comprising nebivolol and/or a salt thereof, preferably nebivolol hydrochloride, in form of a suspension wherein at least about 90% of the suspended particles of nebivolol and/or a pharmaceutically acceptable salt thereof have a size of not more than about 10 µm, after three weeks of storage at room temperature.

In contrast to some other suspensions known in prior art, the pharmaceutical compositions of the present invention when present in the form of a suspension usually require no surfactant, or, if at all, only small amounts of surfactant, for their physical stabilisation. This is a significant advantage as surfactants have a substantial potential for irritation and local toxicity, especially when administered to the eye or by injection. According to one of the preferred embodiments, the pharmaceutical compositions of the invention are substantially free of surfactant. In a further embodiment, the total amount of surfactant or surfactants, if more than one surfactant is incorporated, is not more than about 5% (w/w), in particular not more than about 3% (w/w), or preferably not more than about 1% (w/w), respectively, with regard to the total weight of the final composition. In further preferred embodiments, the amount is not more than about 0.5% (w/w), or not more than about 0.25% (w/w), respectively.

In this context, the semifluorinated alkanes as described herein, although they possess some amphiphilic properties due to their chemical structure which includes fluorinated and non-fluorinated alkyl (or alkylene) groups characterised by different degrees of lipophilicity, are not understood as being within the scope of surfactants.

The surfactants which are absent or only present in small amounts include non-ionic, cationic, anionic, and zwitterionic surfactants as commonly used as excipients in various types of pharmaceutical compositions, e.g. as wetting agents, emulsifiers, dispersing agents, solubilisers and the like. Examples of surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, lecithins, purified or synthetic phospholipids, and mixtures of two or more thereof.

The pharmaceutical composition of the invention may further comprise excipients in range of up to about 10% (w/v), more preferably up to about 5% (w/v), even more preferably up to about 2% (w/v) such as, for example, non-fluorinated organic liquids, for example in order to modify the properties of the liquid vehicle, such as the viscosity. Such other liquid may be an oil selected from glyceride oils, liquid waxes, and liquid paraffin, or an organic solvent exhibiting a high degree of biocompatibility, or a mixture of more than one liquid excipients.

Examples of potentially useful oily excipients which may be used in combination with one or more semifluorinated alkanes as described above may include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

The composition of the present invention may, of course, comprise further pharmaceutical excipients as required or useful. Potentially useful excipients include acids, bases, antioxidants, stabilisers, synergists, colouring agents and thickening agents. In a preferred embodiment, however, the liquid vehicle of the pharmaceutical composition according to the present invention is free of any (further) excipients.

Furthermore, the invention provides a means of formulating pharmaceutical compositions, preferably ophthalmic pharmaceutical compositions comprising nebivolol and/or a pharmaceutically acceptable salt thereof, preferably nebivolol hydrochloride, which are microbiologically stable. This is due to the fact that semifluorinated alkanes as comprised by the liquid vehicle of the present compositions and as described above are not normally prone to microbial contamination. Hence, it is possible to formulate preservative-free ophthalmic compositions which are better tolerable for many patients, in particular patients suffering from an ophthalmic disease or condition. The preservative-free ophthalmic composition may be provided both in multi-dose or single-dose format.

Accordingly, although the pharmaceutical composition of the present invention may comprise a pharmaceutically acceptable preservative, in a preferred embodiment, the pharmaceutical composition of the present invention is free of a preservative. This is especially useful when the composition of the present invention is provided not only in dosage forms for single use (single dosage forms), but especially in multiple dosage forms with a plurality of doses.

In a further embodiment, water can also be present in the pharmaceutical composition of the present invention, however, preferably in small amounts of up 1.0% (w/w) or even of only up to 0.1% (w/w) or less, based on the final composition (final dosage form). In a preferred embodiment, the pharmaceutical composition, preferably the liquid vehicle of the pharmaceutical composition of the present invention is essentially free of water, whereas the residual water may be attributed to the potential residual water content of the active ingredient nebivolol and/or a pharmaceutically acceptable salt thereof, especially nebivolol hydrochloride. The term 'essentially' as used herein means if present then in trace or residual amounts such as to confer no technical advantage or relevance in respect of the object of the invention.

For example, 1-perfluorohexyl-octane (F6H8) or 1-perfluorobutyl-pentane (F4H5) as preferred semifluorinated alkanes in some embodiments of the present invention do not comprise any water, or have a water content of no more than the maximal solubility of water in 1-perfluorohexyl-octane or in 1-perfluorobutyl-pentane; for example 1-perfluorobutyl-pentane has a water-content of less than $1.6 \times 10^{-4}$ mg/ml as determined by methods known in the art for moisture analysis, such as Karl-Fischer titration methods.

In preferred embodiments, the pharmaceutical composition of the present invention essentially consists of nebivolol hydrochloride and a semifluorinated alkane selected from 1-perfluorobutyl-pentane (F4H5) and 1-perfluorohexyl-octane (F6H8). In further embodiments, the pharmaceutical composition of the present invention essentially consists of nebivolol hydrochloride and 1-perfluorohexyl-octane (F6H8), more specifically of nebivolol hydrochloride suspended in 1-perfluorohexyl-octane (F6H8).

In exemplary embodiments, the pharmaceutical composition of the present invention consists of from about 90 to about 99.99% (w/w), more preferably from about 95 to about 99.9% (w/w), more preferably from 97 to 99% (w/w) even more preferably from 98 to 99% (w/w) of the liquid vehicle comprising a semifluorinated alkane as described above, preferably a semifluorinated alkane selected from F4H5 and F6H8, based on the weight of the final composition.

The pharmaceutical composition of the invention in form of liquid suspensions may be prepared by conventional methods. In principle, the solid nebivolol and/or nebivolol salt, preferably nebivolol hydrochloride particles may be suspended in the liquid vehicle comprising the semifluorinated alkane. Alternatively, the particles may be precipitated in situ by adding a—typically organic—solution of the active ingredient (and, optionally, one or more solid excipients) under controlled conditions to the semifluorinated alkane-based vehicle.

Conventional grinding or milling methods using standard equipment such as a ball mill, hammer mill, roller mill, colloidal mill, jet mill, or the like may be used If the particle size is to be reduced after preparation of a suspension, ultrasonication as well as various types of homogenisers may be used, such as colloid mills or high-pressure homogenisers.

In a preferred embodiment, the particle sizes of the solid nebivolol compound in the composition according to the invention, when provided in form of a liquid suspension, are adjusted by first combining the drug particles with a liquid vehicle comprising or consisting of a semifluorinated alkane such as described in any one of the above embodiments, followed by a step of milling or grinding according to any of the above methods.

The pharmaceutical composition comprising a nebivolol compound in suspended form in a liquid vehicle comprising a semifluorinated alkane provides several advantageous properties over conventional, aqueous or not semifluorinated alkane-based formulations, especially with respect to topical administration for ophthalmic use. For example, when conventional perfluorinated compounds are used as liquid vehicles, the suspensions tend to separate very rapidly by flotation of the dispersed phase, or by its sedimentation, depending on the relative densities of the dispersed phase and of the continuous phase. This is accompanied by a rapid formation of particle aggregates which may be dense and poorly re-dispersible. Rapid flotation or sedimentation makes precise and reproducible dosing very challenging, if not impossible. For example, if an ophthalmic suspension settles very rapidly after shaking, the first dosing from a full container, if not withdrawn immediately upon shaking, will contain a lower-than-intended number of drug particles, unless the container is held upside down, in which case more than the intended quantity of drug particles will be dispensed. When the same container is nearly empty and the last doses are dispensed, the drug dose withdrawn per volume will be too high if it was low in the beginning, and vice versa.

Moreover, aggregates may easily obstruct the dispensing channels or openings of containers and thereby lead to erroneous dosing. If dispensed from the container, they may cause irritation of the conjunctiva or of the cornea, depending on their size, shape and hardness.

In contrast, the semifluorinated alkane-based suspensions comprising nebivolol and/or a pharmaceutically acceptable salt thereof according to some embodiments of the invention remain finely dispersed and homogeneous. If flotation or sedimentation takes place, it occurs slowly, leaving sufficient time for the patient to withdraw a dose after shaking the container. The formation of large aggregates is not observed. After flotation or sedimentation, the drug particles are easily re-dispersed by gentle shaking, and appear to largely retain their original particle size distribution. Preferably, the pharmaceutical composition of the present invention is a suspension, wherein the particles of nebivolol and/or a pharmaceutically acceptable salt, preferably nebivolol hydrochloride, are re-dispersible by gentle shaking.

These properties of semifluorinated alkane-based suspensions of nebivolol compounds result in superior pharmaceutical quality and performance characteristics for the use of nebivolol in the treatment of ocular diseases. The level of convenience to the patient and/or health care provider is greatly increased. More importantly, the dosing accuracy, i.e. precision and reproducibility of dosing, is greatly improved over other types of pharmaceutical suspensions. This will bring about a more reliable therapeutic effect and a reduced risk of adverse effects which result from overdosing.

A further surprising advantage of the presently described-compositions in form of suspensions of nebivolol or nebivolol hydrochloride suspended in a semifluorinated alkane is that they appear to form very small droplets when dispensed from a dropper such as an eye dropper. Without wishing to be bound by theory, it is believed that the small droplet size is a result of an interplay of the semifluorinated alkane's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should also contribute to a substantially increased dosing reliability and reproducibility, thus enhancing the safety and effectiveness of the therapy.

A yet further advantage of the invention which is based on the use of semifluorinated alkanes is that they can be designed or mixed for an optimally adjusted evaporation behaviour after administration. Thus, it is possible to formulate an ophthalmic composition which delivers nebivolol or a salt thereof efficiently to the eye in such a way that the liquid vehicles is subsequently eliminated via evaporation. This is in sharp contrast to oily or perfluorinated eye drop vehicles which do easily not evaporate and thus form non-physiological residues at the site of administration, e.g. in the lacrimal sac.

In a second aspect, the present invention provides the pharmaceutical composition according to the first aspect of the invention, namely pharmaceutical composition comprising:
(a) nebivolol and/or a pharmaceutically acceptable salt thereof, and
(b) a liquid vehicle comprising a semifluorinated alkane for use as a medicament.

The pharmaceutical composition including all embodiments thereof as described above for the first aspect of the invention is especially useful for the therapy or prevention of diseases or conditions or any symptoms associated therewith related to an eye of a subject, preferably to an eye of a human subject.

The pharmaceutical composition of the present invention is especially useful as an ophthalmic composition and may be administered to the eye of a subject. More specifically, the pharmaceutical composition of the present invention may be administered topically to the eye of a subject, for example to the eye lid, eye sac, eye surface and/or to an ophthalmic tissue of a patient. Preferably, the pharmaceutical composition of the present invention may be topically administered to an outer surface of an eye of a patient or to an ophthalmic tissue which is readily accessible by the patient or by another person administering the pharmaceutical composition to the eye of the patient in need thereof.

The present pharmaceutical composition, especially when used as liquid of either low or higher viscosity (usually in the range of 1 to 3.5 mPa s) may advantageously be administered in form of drops or by spraying or by injection. Most preferably, however, the liquid pharmaceutical composition of the present invention, especially when provided in the form of a suspension, may be administered as drops, more specifically as eyedrops to be administered topically to the eye.

Depending on the extent of the disease, or whether or not both eyes of the patient to be treated are affected, the drops or eyedrops of the present ophthalmic pharmaceutical compositions may be administered to only one eye or to both eyes of the patient. The present pharmaceutical composition, provides droplet sizes when administered from conventional droppers, with a volume usually in the range from about 5 to about 15 µl. This small droplet size usually facilitates the dropwise administration and, moreover, facilitates precise dosage of the pharmaceutical composition of the present invention. Accordingly, the ophthalmic pharmaceutical composition of the present invention is administered as single drops with a volume of about 5 to 15 µl per dose per eye, preferably with a volume of about 8 to 15 µl per dose per eye, more preferably with a volume of about 9 to 12 µl per dose per eye even more preferably with a volume of about 10 to 12 µl per dose per eye and most preferably with a volume of about 11 µl per dose per eye.

Depending on the need, the composition according to the present invention is administered once (qd), twice (bid), three-times (tid) or four-times (qid) per day per eye. Preferably, the composition according to the present invention is administered up to two-times per day per eye. In a preferred embodiment, the composition of the present invention is administered twice (bid) daily. In a more preferred embodiment, the composition of the present invention is administered once (qd) daily.

The pharmaceutical composition according to the present invention is especially useful in the treatment of glaucoma, increased intraocular pressure (IOP), ocular hypertension and/or a symptom associated therewith.

The present invention provides stable liquid pharmaceutical compositions, especially stable liquid suspensions comprising nebivolol and/or a pharmaceutically acceptable salt thereof, preferably nebivolol hydrochloride. These compositions can be topically administered and allow the administration of the active ingredient nebivolol in lower dosages compared to known liquid formulations, thereby reducing the side effects associated to the active ingredient and the additional components of said known liquid formulations, in particular in the treatment of glaucoma.

Based on this, the pharmaceutical composition for the use of the present invention allows for a significant reduction of droplet size and target dose volume as described above associated therewith and therefore, as outlined above, for a significant reduction of the total daily dose of nebivolol administered for use in the treatment of glaucoma, increased intraocular pressure, ocular hypertension and/or a symptom associated therewith. Accordingly, in preferred embodiments of the present pharmaceutical composition for use in the treatment of glaucoma, increased intraocular pressure (IOP), ocular hypertension and/or a symptom associated therewith, nebivolol and/or a pharmaceutically acceptable salt thereof, preferably of nebivolol hydrochloride, is suspended in the liquid vehicle at a concentration of from 0.3 to 1.5% (w/v) or preferably at a concentration of from 0.5 to 1.0% (w/v). In said preferred embodiments, the liquid vehicle comprises or essentially consists of a semifluorinated alkane, as defined by Formula (II) or any one of the semifluorinated alkanes as defined above, such as a semifluorinated alkane selected from 1-perfluorobutyl pentane or 1-perfluorohexyl octane. In further embodiments, the pharmaceutical composition for the use according to the present invention may be administered in a dose volume per eye of 10 to 12 µl wherein the nebivolol and/or a pharmaceutically acceptable salt thereof may be suspended in the liquid vehicle in a concentration of at least 0.3% (w/v).

In a preferred embodiment of the present invention, the (single) dose of nebivolol and/or pharmaceutically acceptable salt thereof administered per eye is from about 45 to about 120 µg, preferably from about 50 to about 110 µg, even more preferably from about 55 to 110 µg. In a more preferred embodiment, the pharmaceutical composition for use in the treatment of glaucoma, increased intraocular pressure (IOP), ocular hypertension and/or a symptom associated therewith comprises a) nebivolol hydrochloride suspended in a semifluorinated alkane, preferably F6H8, wherein the (single) dose of nebivolol hydrochloride administered per eye is from about 45 to about 120 µg, more preferably from about 50 to about 110 µg, even more preferably from about 55 to 110 µg.

In another embodiment, the pharmaceutical composition for use in the treatment of glaucoma, increased intraocular pressure (IOP), ocular hypertension and/or a symptom associated therewith, is administered to subjects concomitantly suffering from dry eye disease and/or hypertension and/or cardiac related diseases. Thus, the pharmaceutical composition for use in the treatment of glaucoma, increased intraocular pressure (IOP), ocular hypertension and/or a symptom associated therewith, is effective in not exacerbating comorbidities such as dry eye disease and/or hypertension and/or cardiac related diseases.

In another preferred embodiment, the pharmaceutical composition for use in the treatment of glaucoma, increased intraocular pressure (IOP), ocular hypertension and/or a symptom associated therewith is effective in preventing side effects derived from the treatment of glaucoma or ocular hypertension with non-selective beta blockers, wherein said side effects are exacerbation of chronic obstructive airways disease and/or bronchospasm and/or dry eye symptoms. In a third aspect, the present invention provides a method for the treatment of glaucoma, increased intraocular pressure, ocular hypertension and/or a symptom associated therewith, comprising administering to the eye of a subject in need thereof a pharmaceutical composition according to the first aspect of the invention, namely a pharmaceutical composition comprising:

(a) nebivolol and/or a pharmaceutically acceptable salt thereof, and
(b) a liquid vehicle comprising a semifluorinated alkane.

Accordingly, the method according to this aspect of the present invention comprises:
providing a composition comprising:
(a) nebivolol and/or a pharmaceutically acceptable salt thereof, and
(b) a liquid vehicle comprising a semifluorinated alkane, and
topically administering said composition to a surface of the eye of the subject, or the patient.

It should be noted that for the method according to this aspect of the invention all embodiments and preferred embodiments as described above in connection with the other aspects of the invention apply respectively. The subject, or patient in one embodiment may be a human. In another embodiment, the subject may be a veterinary subject or patient.

The pharmaceutical composition according to the present invention offers the possibility to administer and deliver, or to transport the beta 1-receptor blocker nebivolol or a pharmaceutically acceptable salt thereof, especially nebivolol hydrochloride, directly to tissues or liquids of an eye of a subject or patient without the need of systemic application. Especially in cases in which the active compound nebivolol or nebivolol hydrochloride is administered in form of particles, suspended in a liquid vehicle comprising a semifluorinated alkane as described above, high concentrations of the active compound can be delivered in relatively small volumes of the composition.

In yet a further aspect, the present invention provides for the use of the pharmaceutical composition according to the first aspect of the invention, namely a pharmaceutical composition comprising:
(a) nebivolol and/or a pharmaceutically acceptable salt thereof, and
(b) a liquid vehicle comprising a semifluorinated alkane
for the manufacture of a medicament for the treatment of glaucoma, increased intraocular pressure, ocular hypertension and/or a symptom associated therewith.

In yet a further aspect, the present invention provides a pharmaceutical kit comprising the composition as described above in connection with the first aspect of the invention, namely a pharmaceutical composition comprising:

(a) nebivolol and/or a pharmaceutically acceptable salt thereof, and
(b) a liquid vehicle comprising a semifluorinated alkane,
and a container adapted for holding the pharmaceutical composition. Preferably, the container which contains the pharmaceutical composition of the present invention further comprises a drop dispenser or device adapted for administering the pharmaceutical composition.

In specific embodiments of the kit according to this aspect of the present invention, the container has a dispensing means such as a dropping device adapted for topically administering the composition to the eye of a subject or patient, more specifically dispensing means for dropwise topical administration to a surface of the eye of a subject or patient. In one of the preferred embodiments, the dispensing means is adapted to dispense the pharmaceutical composition dropwise in volumes of less than about 15 µl per drop. In further embodiments, the dispensing means is adapted to dispense drops having a volume of less than about 13 µl, 12 µl, or 11 µl, respectively. In particular, drop volumes of less than 12 µl are presently considered very useful in view of the limited holding capacity of one of the preferred sites of administration, the front of the eye. For the avoidance of doubt, such small droplet sizes are primarily enabled by the incorporation of the semifluorinated alkane (or semifluorinated alkanes) according to the invention, and common droppers for eye drops which normally deliver aqueous drops of about 30 to 60 µl are capable of dispensing much smaller drops of semifluorinated alkanes-based formulations.

In the kit according to this aspect of the invention, the container may hold a single dose or a plurality of doses of the present pharmaceutical composition comprising nebivolol and/or a pharmaceutically acceptable salt thereof and a liquid vehicle comprising a semifluorinated alkane as described above.

Furthermore, the kit according to this aspect of the invention may further comprise instructions for use of the container for dropwise topical administration of the composition to a surface of the eye of a patient. The instructions or directions for use preferably comprised by the kit according to this aspect of the invention may be in any form suited to instruct the user how to perform the topical administration to the affected eye of the patient or subject. It may be in any readable or tangible form, preferably in printed form or in any machine- or computer-readable form preferably in form of a machine-readable optical label such as, for example, a barcode or a QR-code. In a particularly preferred embodiment the directions for use are provided in form of an instruction leaflet, product or package insert or as an enclosed label.

DESCRIPTION OF THE DRAWINGS

FIG. 1 is a graphical representation of the results of the measurement of the in-vivo intraocular pressure study according to Example 4 below in which a suspension of nebivolol hydrochloride in 1-perfluorohexyl-octane (F6H8) with a concentration of 0.5% (w/v) is administered versus a formulation of timolol in aqueous solution with a concentration of 0.5% (w/v). The graphs show the chronological progression of the mean intraocular pressure (IOP) as measured in mmHg.

Figure 2:
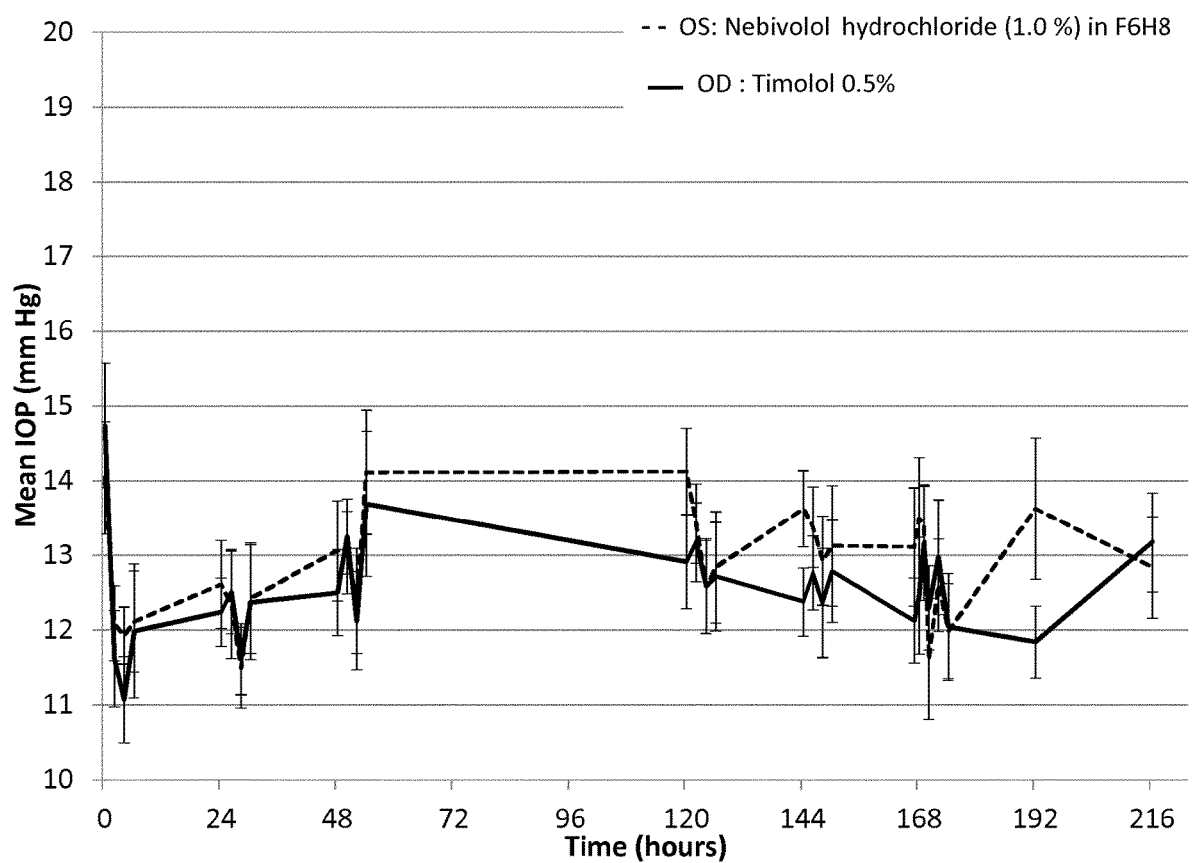
FIG. 2 is a graphical representation of the results of the measurement of the in-vivo intraocular pressure study according to Example 4 below in which a suspension of nebivolol hydrochloride at a concentration of 1.0% (w/v) in 1-perfluorohexyl-octane (F6H8) is administered.

FIG. 2 is a graphical representation of the results of the measurement of the in-vivo intraocular pressure study according to Example 4 below in which a suspension of nebivolol hydrochloride in 1-perfluorohexyl-octane (F6H8)

with a concentration of 1.0% (w/v) is administered versus a formulation of timolol in aqueous solution with a concentration of 0.5% (w/v). The graphs show the chronological progression of the mean intraocular pressure (IOP) as measured in mmHg.

The following are numbered items comprised by the present invention:

1. A pharmaceutical composition comprising:
   (a) nebivolol and/or a pharmaceutically acceptable salt thereof, and
   (b) a liquid vehicle comprising a semifluorinated alkane.
2. The pharmaceutical composition according to item 1, comprising a semifluorinated alkane of the formula (II)

$$CF_3(CF_2)_n(CH_2)_mCH_3 \quad \text{(II)},$$

wherein n is an integer from 2 to 10, and m is an integer from 2 to 10; or
wherein n is an integer from 3 to 5 and m is an integer from 4 to 7

3. The pharmaceutical composition of item 1 or 2, wherein the semifluorinated alkane is selected from the group consisting of 1-perfluorobutyl-pentane ($CF_3(CF_2)_3(CH_2)_4CH_3$; F4H5) and 1-perfluorohexyl-octane ($CF_3(CF_2)_5(CH_2)_7CH_3$, F6H8).
4. The pharmaceutical composition of any preceding item, wherein the liquid vehicle comprises a co-solvent.
5. The pharmaceutical composition of any preceding item, wherein the liquid vehicle comprises at least 85% (w/w) of a semifluorinated alkane or a mixture of different semifluorinated alkanes.
6. The pharmaceutical composition of any preceding item, wherein the liquid vehicle essentially consists of a semifluorinated alkane or a mixture of different semifluorinated alkanes.
7. The pharmaceutical composition of any preceding item, wherein the nebivolol and/or a pharmaceutically acceptable salt thereof is suspended in the liquid vehicle comprising a semifluorinated alkane.
8. The pharmaceutical composition of any preceding item, wherein nebivolol and/or a pharmaceutically acceptable salt thereof is suspended in the liquid vehicle at a concentration of from 0.3 to 1.5% (w/v).
9. The pharmaceutical composition of any preceding item, wherein nebivolol and/or a pharmaceutically acceptable salt thereof is suspended in the liquid vehicle at a concentration of from 0.45 to 1.0% (w/v).
10. The pharmaceutical composition of any preceding item, comprising nebivolol in the form of nebivolol hydrochloride.
11. The pharmaceutical composition of any preceding item, wherein the composition is essentially free of water and/or a preservative.
12. The composition of any preceding item, wherein the composition is free of further excipients.
13. The composition of any preceding item, wherein the composition is free of a surfactant.
14. The pharmaceutical composition of any preceding item, wherein the composition essentially consists of nebivolol hydrochloride and a semifluorinated alkane selected from 1-perfluorobutyl-pentane (F4H5) and 1-perfluorohexyl-octane (F6H8).
15. The pharmaceutical composition of any preceding item, wherein the composition essentially consists of nebivolol hydrochloride and 1-perfluorohexyl-octane (F6H8).
16. The pharmaceutical composition of any of item 7 to 15, wherein at least about 90% of the suspended particles of nebivolol and/or a pharmaceutically acceptable salt thereof have a size of not more than about 15 μm, or not more than about 10 μm.
17. The pharmaceutical composition of any of item 7 to 16, wherein at least about 90% of the suspended particles of nebivolol and/or a pharmaceutically acceptable salt thereof have a size of not more than about 10 μm after three weeks of storage at room temperature.
18. The pharmaceutical composition of any preceding item for use as a medicament.
19. The pharmaceutical composition for use according to item 18, for the treatment of glaucoma, increased intraocular pressure, ocular hypertension and/or a symptom associated therewith.
20. The pharmaceutical composition for use according to item 18 or 19, wherein the composition is administered to the eye of a subject.
21. The pharmaceutical composition for use according to any of items 18 to 20, wherein the composition is administered topically to the eye of a subject.
22. The pharmaceutical composition for the use according to any of items 18 to 21, wherein the pharmaceutical composition is administered in a dose volume per eye, of 8 to 15 μl, preferably from about 10 to 12 μl.
23. The pharmaceutical composition for use according to any of items 18 to 22, wherein the pharmaceutical composition is administered in a dose volume per eye of 10 to 12 μl and nebivolol and/or a pharmaceutically acceptable salt thereof is suspended in the liquid vehicle in a concentration of at least 0.3% (w/v).
24. The pharmaceutical composition for the use according to any of items 18 to 23, wherein nebivolol and/or a pharmaceutically acceptable salt thereof is suspended in the liquid vehicle in a concentration of from 0.45 to 1.0% (w/v).
25. The pharmaceutical composition for the use according to any of items 18 to 24, wherein the composition is administered up to two times (bid) daily, preferably the composition is administered once daily.
26. A method for the treatment of glaucoma, increased intraocular pressure, ocular hypertension and/or a symptom associated therewith, comprising administering to the eye of a subject in need thereof a pharmaceutical composition according to any one of items 1 to 17.
27. The use of a pharmaceutical composition of any of items 1 to 17 for the manufacture of a medicament for the treatment of glaucoma, increased intraocular pressure, ocular hypertension and/or a symptom associated therewith.
28. A kit comprising the pharmaceutical composition according to any one of items 1 to 17 and a container for holding the pharmaceutical composition.
29. The kit according to item 28, wherein the container comprises a drop dispenser for administering the pharmaceutical composition.
30. The kit according to item 29, wherein the container comprises dispensing means for dropwise topical administration to a surface of the eye of a patient, said dispensing means preferably being adapted to dispense the composition dropwise in volumes of less than about 15 μl.
31. The kit according to any of item 28 to 30, wherein the container holds a single dose or a plurality of doses of the composition of any of claims 1 to 17.
32. The kit according to any of items 28 to 31, further comprising instructions for use of the container for dropwise topical administration of the composition to a surface of the eye of a patient.

33. A method of treating glaucoma, increased intraocular pressure, ocular hypertension or a symptom associated therewith, the method comprising administering to an eye of a human with glaucoma, increased intraocular pressure, ocular hypertension or a symptom associated therewith, a composition comprising a) nebivolol and/or a pharmaceutically acceptable salt thereof and b) a liquid vehicle comprising a semifluorinated alkane, wherein the nebivolol and/or pharmaceutically acceptable salt thereof is preferably suspended in the liquid vehicle, wherein the amount of nebivolol and/or pharmaceutically acceptable salt thereof administered in a single dose per eye is from about 45 to about 120 µg, and wherein said method is therapeutically effective in treating glaucoma, increased intraocular pressure, ocular hypertension or a symptom associated therewith.
34. The method according to item 33, wherein the composition target dose volume per eye is from about 8 to about 15 µl.
35. The method according to any one of items 33 to 34, wherein the composition target dose volume per eye is from about 10 to about 12 µl, preferably about 11 µl.
36. The method according to any one of items 33 to 35, wherein the composition comprises from about 0.45% to 1.0% w/v nebivolol and/or a pharmaceutically acceptable salt thereof; and wherein the nebivolol and/or a pharmaceutically acceptable salt thereof administered in a single dose per eye is about 55 to about 110 µg and the target dose volume per eye is about 11 µl.
37. The method according to any of items 33 to 36, wherein the semifluorinated alkane is selected from F6H8 and F4H5.
38. The method according to item 37, wherein the semifluorinated alkane is F6H8.
39. The method according to any one of items 33 to 38, wherein the composition is administered once daily.
40. The method according to any one of items 33 to 39, wherein the composition is substantially free of water and of preservative.
41. The method according to any one of items 33 to 40, wherein the composition comprises nebivolol in form of nebivolol hydrochloride.

The following examples serve to illustrate the invention; however, these are not to be understood as restricting the scope of the invention.

EXAMPLES

Example 1: Preparation of Nebivolol Suspensions 80 mg of nebivolol-hydrochloride (Sigma Aldrich; purity 100%) were introduced to a 25 mL vessel, filled with stainless steel balls, diameter 2 mm. Afterwards, 8 mL of 1-perfluorohexyl-octane (F6H8) were added, the vessel was closed and the milling was performed with a planetary ball mill (PM 100, Retsch GmbH Germany) for 3 hours at 150 rpm with an interval of 10 minutes (with change of direction). After the milling, the thereby formed suspension was transferred into a glass vial, shaken on a Vortex shaker for a minimum of 30 seconds, and sealed. Hereby, a 1.0% (w/v) Nebivolol-hydrochloride suspension (10 mg/mL) in F6H8 was obtained.

According to the same procedure a 1.0% (w/v) nebivolol-hydrochloride suspension (10 mg/mL) in 1-perfluorobutyl-pentane (F4H5) was prepared using 8 mL of F4H5 instead of F6H8.

The 10 mg/mL nebivolol suspension was stored in a glass vial at room temperature and the particle size distribution (PSD) was determined by Laser diffraction (HELOS 2412, performed with a 50 mL cuvette). Table 1 below shows the particle size distributions for different Nebivolol suspensions after storage of one day at room temperature.

TABLE 1

| Formulation | $X_{50}$ (µM) | $X_{90}$ (µm) | $X_{99}$ (µm) |
|---|---|---|---|
| Nebivolol hydrochloride 10 mg/mL in F6H8 | 3.58 | 8.69 | 13.20 |
| Nebivolol hydrochloride 10 mg/mL in F4H5 | 3.48 | 8.28 | 12.88 |

$X_{50}$: median particle diameter determined on a volumetric basis, i.e. 50% by volume of the particles are smaller than the given diameter and 50% are larger.

$X_{90}$: particle diameter corresponding to 90% of the cumulative undersize distribution determined on a volumetric basis, i.e. 90% of the particles have a diameter lower than the given value $X_{90}$.

$X_{99}$: particle diameter corresponding to 99% of the cumulative undersize distribution determined on a volumetric basis, i.e. 99% of the particles have a diameter lower than the given value $X_{99}$.

Example 2: Stability Assessment of Nebivolol Suspensions

The Nebivolol suspensions as prepared according to Example 1 above were stored for 3 weeks at room temperature (20-25° C.). Following that, the particle size distribution (PSD) was re-investigated by Laser diffraction (Helios 2412, performed with a 50 mL cuvette) and microscopic analysis. Table 2 below shows the particle size distributions for different nebivolol suspensions after 3 weeks storage at room temperature (20-25° C.).

TABLE 2

| Formulation | $X_{50}$ (µM) | $X_{90}$ (µm) | $X_{99}$ (µm) |
|---|---|---|---|
| Nebivolol hydrochloride 10 mg/mL in F4H5 | 3.81 | 9.71 | 15.35 |
| Nebivolol hydrochloride 10 mg/mL in F6H8 | 3.46 | 8.12 | 12.56 |

Example 3: Dilution Experiments of Nebivolol Suspensions

Nebivolol suspensions in F4H5 or F6H8 with a concentration of 10 mg/mL were prepared according to Example 1 above using Nebivolol-hydrochloride (CAS No. 152520-56-4; Chemos GmbH&Co. KG, Regenstauf). The suspensions were diluted to concentration of 5 mg/mL by addition of an aliquot of either F4H5 or F6H8. The resulting suspensions were homogenous after preparation upon visual inspection and were stored at room temperature for 5 days. After that, the suspensions were separated and cloudy, however, resuspension of the settled suspensions was easily achieved.

After 5 days of storage at room temperature (20-25° C.) the particle size distribution was determined by laser diffraction (HELOS 2412, performed with a 50 mL cuvette) as summarized in Table 3 below.

TABLE 3

| Formulation | $X_{50}$ (μM) | $X_{90}$ (μm) | $X_{99}$ (μm) |
|---|---|---|---|
| Nebivolol hydrochloride 10 mg/mL in F6H8 | 3.59 | 7.32 | 16.46 |
| Nebivolol hydrochloride 5 mg/mL in F6H8 | 3.46 | 8.23 | 22.95 |

All Nebivolol hydrochloride suspensions in pure F4H5 and F6H8 with concentrations of 5 mg/ml and 10 mg/mL, respectively, prepared by a ball milling process as described above showed an optical appearance, homogeneity of the suspension and a suitability for re-homogenization of the settled suspensions which were ranked positive for preclinical studies in animal models.

The stability of the Nebivolol hydrochloride 5 mg/mL suspension formulation in F6H8 was studied over 8 weeks. Samples were stored at room temperature in closed glass vials. The appearance and the particle size distribution, measured via microscope and DLS, did not change.

The stability of the corresponding Nebivolol hydrochloride 10 mg/ml formulation in F6H8 was conducted with the same design over 4 weeks. No significant changes were detected.

Example 4: Measurement of Intraocular Pressure (IOP) in an Animal Study

An animal study utilizing normotensive dogs was carried out in order to assess the pharmacodynamics of Nebivolol with regard to its capability to lower the IOP (intraocular pressure) in comparison to the non-selective beta-blocker Timolol which is administered in form of an aqueous solution. The study setup and design was as follows:

A total number of eight dogs were selected for participation in the study based on overall health, body weight, results of ophthalmic examinations, response to IOP challenge, and the following criteria:

healthy, normal ocular surface;

no invasive ocular procedures for at least one month prior to the study; particularly procedures involving the cornea or ocular anterior segment in general;

no topical or systemic corticosteroid treatment for at least one month;

washout from prior topical ocular study medication commensurate with the typical washout period used for clinical studies (at least one week)

The study was performed according to the plan as summarized in Table 4 below. The topical ocular dose of the respective Timolol-solution or Nebivolol-suspension was administered to the central or superior part of the cornea via a micropipette and allowed to spread across the surface of the eye. After the dose was administered, the eye was allowed to close naturally. Each animal was restrained for approximately one minute to prevent rubbing of the eyes.

TABLE 4

| Topical Ocular Dose Regime | | Target Dose Level (μg/eye) | | Target Dose Volume (μL/eye) | Dose Frequency | Measurement/ Samples Collected |
|---|---|---|---|---|---|---|
| OD | OS | OD | OS | | | |
| Timolol 0.5% (=5 mg/mL)* | Nebivolol hydrochloride in F6H8 (5 mg/mL) | 150 | 55 | 11 (OS) 30 (OD) | QD for 8 days | IOP and Irritation scoring |
| Timolol 0.5% (=5 mg/mL)* | Nebivolol hydrochloride (10 mg/mL) | 150 | 110 | 11 (OS) 30 (OD) | QD for 8 days | IOP and Irritation scoring | d Days
IOP Intraocular pressure
OD Right eye
OS Left eye
QD Once daily
*aqueous solution In a first study, a suspension of Nebivolol hydrochloride in F6H8 (5 mg/mL, translating to 4.6 mg/ml Nebivolol) was administered to the left eye (OS) versus an aqueous solution of Timolol (5 mg/mL) which was administered to the right eye. Administration was done once daily for 8 days. The intraocular pressure (IOP) was measured at 0 (immediately pre-dose), 2, 4 and 6 hours post-dose on days 1, 2, 3, 6 and 7; at −1, 0 (immediately pre-dose), 1, 2, 4, 6, 24 and 48 hours post-dose on day 8 using a tonometer (TonoVet). Three readings per eye were taken. The results are summarized in FIG. 1 showing the development of the mean intraocular pressure (IOP) during treatment as described above.

In a second study, a suspension of Nebivolol hydrochloride in F6H8 (10 mg/mL; translating to 9.2 mg/ml Nebivolol) was administered to the left eye (OS) versus an aqueous solution of Timolol (5 mg/mL) which was administered to the right eye. Administration was done once daily for 8 days. The intraocular pressure (IOP) was measured at 0 (immediately pre-dose), 2, 4 and 6 hours post-dose on days 1, 2, 3, 6, and 7; at −1, 0 (immediately pre-dose), 1, 2, 4, 6, 24 and 48 hours post-dose on day 8 using a tonometer (TonoVet). Three readings per eye were taken. The results are summarized in FIG. 2 showing the development of the mean intraocular pressure (IOP) during treatment as described above.

Study Analysis

As shown in FIG. 1, the administration of 11 μl of 5 mg/ml nebivolol hydrochloride in F6H8 (50.5 μg nebivolol, 0.12 μmol) resulted in a decrease of the intraocular pressure comparable to that of solutions of 5 mg/ml timolol (150 μg timolol, 0.47 μmol) administered in a target dose volume per eye of 30 μl.

The experimental data shows that by using a composition according to the present invention it is possible to achieve a decrease of the IOP comparable to that of a commercial solution of a non-selective beta blocker even with using a lower target dose of the active ingredient (0.12 mmol nebivolol vs 0.47 µmol timolol), translating to a reduction of the administered single dose per eye of about 74%. Furthermore, the lower target dose can be administered in a volume of, for example 11 µl, i.e. in a volume considerably lower than 30 µl, thus allowing a reduction of the amount of composition which is expelled or which is taken up systemically.

As shown in FIG. 2, the administration of 11 µl of 10 mg/ml nebivolol hydrochloride in F6H8 (100.9 µg nebivolol, 0.25 µmol) resulted in a decrease of the intraocular pressure comparable to that of solutions of 5 mg/ml timolol (150 µg timolol, 0.47 µmol) administered in a target dose volume per eye of 30 µl.

The invention claimed is:

1. A pharmaceutical composition consisting essentially of:
   (a) nebivolol and/or a pharmaceutically acceptable salt thereof, and
   (b) a semifluorinated alkane;
   wherein the nebivolol and/or a pharmaceutically acceptable salt thereof is suspended in the semifluorinated alkane, and wherein at least 90% of the suspended particles of nebivolol and/or a pharmaceutically acceptable salt thereof have a size of not more than about 15 µm.

2. The pharmaceutical composition according to claim 1, wherein the semifluorinated alkane is a semifluorinated alkane of the formula (II)

$$CF_3(CF_2)_n(CH_2)_mCH_3 \qquad (II)$$

wherein n is an integer from 2 to 10 and m is an integer from 2 to 10; or
   wherein n is an integer from 3 to 5 and m is an integer from 4 to 7.

3. The pharmaceutical composition of claim 1, wherein the semifluorinated alkane is selected from the group consisting of 1-perfluorobutyl-pentane ($CF_3(CF_2)_3(CH_2)_4CH_3$; F4H5) and 1-perfluorohexyl-octane ($CF_3(CF_2)_5(CH_2)_7CH_3$, F6H8).

4. The pharmaceutical composition of claim 1, wherein the pharmaceutically acceptable salt of nebivolol is suspended in the semifluorinated alkane.

5. The pharmaceutical composition of claim 1, wherein the nebivolol and/or a pharmaceutically acceptable salt thereof is suspended in the semifluorinated alkane at a concentration of from 0.3 to 1.5% (w/v).

6. The pharmaceutical composition of claim 1, wherein the nebivolol and/or a pharmaceutically acceptable salt thereof is suspended in the semifluorinated alkane at a concentration of from 0.45 to 1.0% (w/v).

7. The pharmaceutical composition of claim 1, wherein the nebivolol is in the form of nebivolol hydrochloride.

8. The pharmaceutical composition of claim 1, wherein at least about 90% of the suspended particles of nebivolol and/or a pharmaceutically acceptable salt thereof have a size of not more than about 10 µm.

9. The pharmaceutical composition of claim 1, wherein the composition is essentially free of water.

10. The pharmaceutical composition of claim 1, wherein the composition is preservative-free and microbiologically stable.

11. The pharmaceutical composition of claim 10, provided in a multi-dose or single dose format.

12. The pharmaceutical composition of claim 1, wherein the composition consists essentially of nebivolol hydrochloride and a semifluorinated alkane selected from F4H5, F4H6, F4H7, F4H8, F5H5, F5H6, F5H7, F5H8, F6H5, F6H6, F6H7, F6H8, F8H8, and F6H10.

13. The pharmaceutical composition of claim 12, wherein the composition consists essentially of nebivolol hydrochloride and a semifluorinated alkane selected from 1-perfluorobutyl-pentane (F4H5) and 1-perfluorohexyl-octane (F6H8).

14. The pharmaceutical composition of claim 1, wherein the composition is essentially free of water, preservative-free, and substantially free of surfactant.

15. A kit comprising the pharmaceutical composition according to claim 1, and a container for holding the pharmaceutical composition.

16. A method for the treatment of glaucoma, increased intraocular pressure, ocular hypertension and/or a symptom associated therewith, comprising administering to a patient in need thereof a composition according to claim 1.

17. The method according to claim 16, wherein the composition is administered to the eye of a subject once daily.

18. The method according to claim 17, wherein the composition is administered to the eye of a subject in a single dose from about 45 to about 120 µg.

19. The method according to claim 16, wherein the pharmaceutical composition is administered in a dose volume per eye of 8 to 15 µl.

20. The method according to claim 16, wherein the pharmaceutical composition is administered in a dose volume per eye of 10 to 12 µl and wherein the composition comprises the nebivolol and/or a pharmaceutically acceptable salt thereof suspended in the semifluorinated alkane in a concentration of at least 0.3% (w/v).

21. The method according to claim 16, wherein the composition comprises the nebivolol and/or a pharmaceutically acceptable salt thereof suspended in the semifluorinated alkane in a concentration of from 0.45 to 1.0% (w/v).

* * * * *